(12) United States Patent
Marcos et al.

(10) Patent No.: US 10,973,407 B2
(45) Date of Patent: Apr. 13, 2021

(54) METHOD FOR DETERMINING AN OPHTHALMIC LENS HAVING UNWANTED ASTIGMATISM

(71) Applicant: Essilor International, Charenton-le-Pont (FR)

(72) Inventors: Susana Marcos, Madrid (ES); Carlos Dorronsoro, Madrid (ES); Mirian Velasco, Madrid (ES); Martha Hernandez, Charenton-le-Pont (FR); Laurent Calixte, Charenton-le-Pont (FR); Gildas Marin, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 373 days.

(21) Appl. No.: 15/558,225

(22) PCT Filed: Mar. 14, 2016

(86) PCT No.: PCT/EP2016/055463
§ 371 (c)(1),
(2) Date: Sep. 14, 2017

(87) PCT Pub. No.: WO2016/146590
PCT Pub. Date: Sep. 22, 2016

(65) Prior Publication Data
US 2018/0042474 A1   Feb. 15, 2018

(30) Foreign Application Priority Data
Mar. 18, 2015 (EP) .................................. 15305396

(51) Int. Cl.
*A61B 3/10* (2006.01)
*A61B 3/103* (2006.01)
(Continued)

(52) U.S. Cl.
CPC ............ *A61B 3/1035* (2013.01); *G02C 7/027* (2013.01); *G02C 7/04* (2013.01); *G02C 7/063* (2013.01);
(Continued)

(58) Field of Classification Search
CPC ........ A61B 3/1035; G02C 7/063; G02C 7/04; G02C 7/027; G02C 7/061; G02C 7/028;
(Continued)

(56) References Cited

U.S. PATENT DOCUMENTS 6,318,859 B1   11/2001 Baudart et al.
2012/0008089 A1 *   1/2012 Kozu ...................... G02C 7/02
703/1

(Continued)

OTHER PUBLICATIONS

International Search Report and Written Opinion dated Mar. 6, 2016 in PCT/EP2016/055463.
(Continued)

*Primary Examiner* — William R Alexander
*Assistant Examiner* — Henry A Duong
(74) *Attorney, Agent, or Firm* — Oblon, McClelland, Maier & Neustadt, L.L.P.

(57) ABSTRACT

A method for determining an ophthalmic lens having unwanted astigmatism, the ophthalmic lens being adapted to a wearer, the method including: a wearer prescription data providing during which wearer prescription data indicative of an ophthalmic prescription of the wearer are provided; a wearer focal data providing during which wearer focal data indicative of the wearer preferred image focal plan are provided; an ophthalmic lens determining during which the ophthalmic lens is determined based on the prescription of the wearer and the wearer focal data to reduce impact of unwanted astigmatism of the ophthalmic lens for the wearer.

12 Claims, 9 Drawing Sheets

(51) Int. Cl.
*G02C 7/02* (2006.01)
*G02C 7/06* (2006.01)
*G02C 7/04* (2006.01)
*A61F 2/16* (2006.01)

(52) U.S. Cl.
CPC ............ *A61F 2/1624* (2013.01); *G02C 7/028* (2013.01); *G02C 7/061* (2013.01)

(58) Field of Classification Search
CPC .. G02C 7/02; G02C 2202/10; G02C 2202/22; A61F 2/1624
USPC .................................................... 351/159.52
See application file for complete search history.

(56) References Cited

U.S. PATENT DOCUMENTS

2012/0057122 A1\* 3/2012 Guillot ............... G02B 27/0172
351/159.74
2017/0371181 A1\* 12/2017 Kaga ........................ G02C 7/02

OTHER PUBLICATIONS

Janine Buttner et al., "Die Kreuzzylindermethode-Grenzen und Moglichkeiten, Teil 1", Deutsche Optikerzeitung, vol. Oct. 2012, XP055208645, Oct. 1, 2012, pp. 50-53.

\* cited by examiner

METHOD FOR DETERMINING AN OPHTHALMIC LENS HAVING UNWANTED ASTIGMATISM

FIELD OF THE INVENTION

The invention relates to a method, for example implemented by computer means, for determining an ophthalmic lens having unwanted astigmatism, the ophthalmic lens being adapted to a wearer. The invention further relates to a set of ophthalmic lenses and to a system for determining an ophthalmic lens having unwanted astigmatism and being adapted to a wearer.

BACKGROUND OF THE INVENTION

Usually, when determining an ophthalmic lens adapted for a wearer, prescription data are considered. The ophthalmic lenses, in particular progressive additional ophthalmic lenses may comprise unwanted astigmatism resulting from the optical design of the ophthalmic lens. The lens designer may modify the optical design so as to try to reduce the unwanted astigmatism however in some cases such unwanted astigmatism cannot be totally avoided or reducing the unwanted astigmatism requires reducing the optical performance of the optical lens.

Therefore there is a need for a method for determining an ophthalmic lens having unwanted astigmatism and adapted for a wearer so as to reduce the impact of the unwanted astigmatism of the ophthalmic lens for the wearer.

One object of the present invention is to provide such a method.

SUMMARY OF THE INVENTION

To this end, the invention proposes a method, for example implemented by computer means, for determining an ophthalmic lens having unwanted astigmatism, the ophthalmic lens being adapted to a wearer, wherein the method comprises:
- a wearer prescription data providing step during which wearer prescription data indicative of the ophthalmic prescription of the wearer are provided,
- a wearer focal data providing step during which wearer focal data indicative of the wearer preferred image focal plan are provided,
- a ophthalmic lens determining step during which the ophthalmic lens is determined based on the prescription of the wearer and the wearer focal data so as to reduce the impact of the unwanted astigmatism of the ophthalmic lens for the wearer.

Advantageously, determining the ophthalmic lens based on the wearer focal data allows reducing the impact of the unwanted astigmatism for the wearer.

The inventors have found that the position of the wearer preferred image focal plan, when the ophthalmic lens has unwanted astigmatism, does not always correspond to the circle of least confusion.

Indeed, the inventors have observed that the position of the wearer preferred image focal plan shifts, for example according to the ametropia of the wearer, within the Sturm's interval.

The method according to the invention proposes to consider this effect to limit the impact of unwanted astigmatism for the wearer, thus extending the subjective field of vision and/or wearer visual acuity when wearing a lens having unwanted astigmatism.

According to further embodiments which can be considered alone or in combination:
- during the ophthalmic lens determining step the spherical power of the ophthalmic lens in at least one gaze direction $(\alpha i, \beta i)$ is determined based on the prescription of the wearer and the position of the wearer preferred image focal plan so as to reduce the impact of the unwanted astigmatism of the ophthalmic lens for the wearer; and/or
- during the ophthalmic lens determining step the spherical power of the ophthalmic lens is determined so that the distance between the wearer preferred image focal plan and the retina of the wearer is reduced; and/or
- the ophthalmic lens has an unwanted astigmatism of horizontal axis in at least one gaze direction $(\alpha i, \beta i)$ and during the ophthalmic lens determining step for the at least one gaze direction $(\alpha i, \beta i)$:
  - the spherical power of the ophthalmic lens is increased relative to spherical power based on the ophthalmic prescription of the wearer when the wearer preferred image focal plan corresponds to a vertical preference; and
  - the spherical power of the ophthalmic lens is reduced relative to spherical power based on the ophthalmic prescription of the wearer when the wearer preferred image focal plan corresponds to a horizontal preference; and/or
- the ophthalmic lens has an unwanted astigmatism of vertical axis in at least one gaze direction $(\alpha i, \beta i)$ and during the ophthalmic lens determining step for the at least one gaze direction $(\alpha i, \beta i)$:
  - the spherical power of the ophthalmic lens is reduced relative to spherical power based on the ophthalmic prescription of the wearer when the wearer preferred image focal plan corresponds to a vertical preference; and
  - the spherical power of the ophthalmic lens is increased relative to spherical power based on the ophthalmic prescription of the wearer when the wearer preferred image focal plan corresponds to a horizontal preference; and/or
- the method further comprises:
  - an initial optical function Fi providing step, during which an initial optical function comprising for each gaze direction $(\alpha i, \beta i)$ of a set of gaze directions S $((\alpha 1, \beta 1); (\alpha 2, \beta 2); \ldots ; (\alpha n, \beta n))$, a value of unwanted astigmatism ASRi and a value of spherical power Pi is provided,
  - an target optical function determining step, during which an target optical function Ft comprising for each gaze direction $(\alpha i, \beta i)$ of a set of gaze directions S $((\alpha 1, \beta 1); (\alpha 2, \beta 2); \ldots ; (\alpha n, \beta n))$, a target value of unwanted astigmatism ASRt and a target value of spherical power Pt is determined with ASRt=ASRi and Pt=Pi+Corr,
  - Corr being a spherical power corrective value based at least on the wearer focal data; and
  - during the ophthalmic lens determining step the ophthalmic lens is determined based on the target optical function and/or
- the initial optical function Fi is determined based on the ophthalmic prescription of the wearer; and/or
- the wearer prescription data comprise a cylinder prescription value and the spherical power corrective value Corr is determined based at least on the cylinder prescription value; and/or the wearer prescription data comprise a cylinder prescription axis value and the spherical power corrective value Corr is determined based at least on the cylinder prescription axis value; and/or the wearer prescription data comprise a sphere prescription value and the spherical power corrective value Corr is determined based at least on the sphere prescription value.

According to a further aspect, the invention relates to a method for determining the wearer preferred image focal plan when wearing an ophthalmic lens having unwanted astigmatism, the method comprising:

an optical lens providing step during which an optical lens having controlled cylinder power and axis is provided to the wearer, a wearer preferred image focal plan position determining step during which the position of the wearer preferred image focal plan is determined by adjusting the position of the image plan until the position indicated by the wearer as preferred is reached.

The invention further relates to a set of ophthalmic lenses having the same prescription, the set of ophthalmic lenses comprising at least a first ophthalmic lens and a second ophthalmic lens wherein for each gaze direction ($\alpha i, \beta i$) the difference of unwanted astigmatism between the first and second ophthalmic lenses is smaller than or equal to 0.12 D and over a group of gaze directions corresponding for each of the first and second ophthalmic lenses, to a unwanted astigmatism greater than 0.75 D, the difference of spherical power between the first and second ophthalmic lenses is greater than or equal to 0.12 D.

The invention also relates to a system for determining an ophthalmic lens having unwanted astigmatism adapted to a wearer, comprising:

a non-transitory computer-readable medium;

program instructions stored on the non-transitory computer-readable medium and executable by at least one processor to:

receive wearer prescription data indicative of the ophthalmic prescription of the wearer, receive wearer focal data indicative of the wearer preferred image focal plan, determine the ophthalmic lens based on the prescription of the wearer and the wearer focal data so as to reduce the impact of the unwanted astigmatism of the ophthalmic lens for the wearer.

The invention further relates to a computer program product comprising one or more stored sequences of instructions that are accessible to a processor and which, when executed by the processor, causes the processor to carry out the steps of the methods according to the invention.

The invention also relates to a computer-readable storage medium having a program recorded thereon; where the program makes the computer execute the method of the invention.

The invention further relates to a device comprising a processor adapted to store one or more sequence of instructions and to carry out at least one of the steps of the method according to the invention.

Unless specifically stated otherwise, as apparent from the following discussions, it is appreciated that throughout the specification discussions utilizing terms such as "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. These apparatuses may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

BRIEF DESCRIPTION OF THE DRAWINGS

Embodiments of the invention will now be described, by way of example only, and with reference to the following drawings in which.

Figure 1:
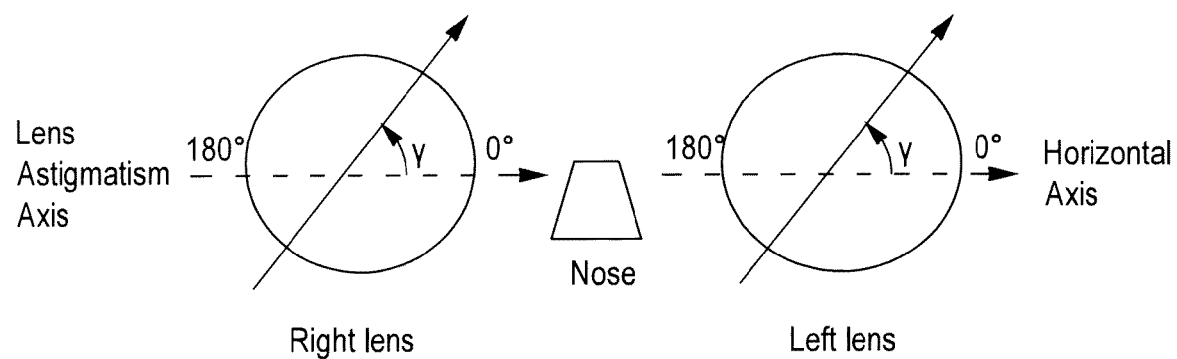
FIG. 1 illustrates the astigmatism axis $\gamma$ of a lens in the TABO convention.

In the sense of the invention, an optical function corresponds to a function providing for each gaze direction the effect of an optical lens on the light ray passing through the optical lens.

The optical function may comprise dioptric function, light absorption, polarizing capability, reinforcement of contrast capacity, etc. . . . .

The dioptric function corresponds to the optical lens power (mean power, astigmatism etc. . . . ) as a function of the gaze direction.

The wording "optical design" is a widely used wording known from the man skilled in the art in ophthalmic domain to designate the set of parameters allowing to define a dioptric function of an ophthalmic lens; each ophthalmic lens designer has its own designs, particularly for progressive ophthalmic lenses. As for an example, a progressive ophthalmic lens "design" results of an optimization of a progressive surface so as to restore a presbyope's ability to see clearly at all distances but also to optimally respect all physiological visual functions such as foveal vision, extrafoveal vision, binocular vision and to minimize unwanted astigmatisms. For example, a progressive lens design comprises:

a power profile along the main gaze directions (meridian line) used by the lens wearer during day life activities, distributions of powers (mean power, astigmatism, . . . ) on the sides of the lens, that is to say away from the main gaze direction.

These optical characteristics are part of the "designs" defined and calculated by ophthalmic lens designers and that are provided with the progressive lenses.

Although the invention is not limited to progressive lenses, the wording used is illustrated in FIGS. 1 to 10 for a progressive lens. The skilled person can adapt the definitions in case of single vision lenses.

A progressive lens comprises at least one but preferably two non-rotationally symmetrical aspheric surfaces, for instance but not limited to, progressive surface, regressive surface, toric or atoric surfaces.

As is known, a minimum curvature $CURV_{min}$ is defined at any point on an aspherical surface by the formula:

$$CURV_{min} = \frac{1}{R_{max}}$$

where $R_{max}$ is the local maximum radius of curvature, expressed in meters and $CURV_{min}$ is expressed in dioptres.

Similarly, a maximum curvature $CURV_{max}$ can be defined at any point on an aspheric surface by the formula:

$$CURV_{max} = \frac{1}{R_{min}}$$

where $R_{min}$ is the local minimum radius of curvature, expressed in meters and $CURV_{max}$ is expressed in dioptres.

It can be noticed that when the surface is locally spherical, the local minimum radius of curvature $R_{min}$ and the local maximum radius of curvature $R_{max}$ are the same and, accordingly, the minimum and maximum curvatures $CURV_{min}$ and $CURV_{max}$ are also identical. When the surface is aspherical, the local minimum radius of curvature $R_{min}$ and the local maximum radius of curvature $R_{max}$ are different.

From these expressions of the minimum and maximum curvatures $CURV_{min}$ and $CURV_{max}$, the minimum and maximum spheres labeled $SPH_{min}$ and $SPH_{max}$ can be deduced according to the kind of surface considered.

When the surface considered is the object side surface (also referred to as the front surface), the expressions are the following:

$$SPH_{min} = (n-1) * CURV_{min} = \frac{n-1}{R_{max}},$$

$$\text{and } SPH_{min} = (n-1) * CURV_{min} = \frac{n-1}{R_{max}}$$

where n is the index of the constituent material of the lens.

If the surface considered is an eyeball side surface (also referred to as the back surface), the expressions are the following:

$$SPH_{min} = (1-n) * CURV_{min} = \frac{1-n}{R_{max}},$$

$$\text{and } SPH_{max} = (1-n) * CURV_{max} = \frac{1-n}{R_{min}}$$

where n is the index of the constituent material of the lens.

As is well known, a mean sphere $SPH_{mean}$ at any point on an aspherical surface can also be defined by the formula:

$$SPH_{mean} = \frac{1}{2}(SPH_{min} + SPH_{max})$$

The expression of the mean sphere therefore depends on the surface considered:

if the surface is the object side surface, $$SPH_{mean} = \frac{n-1}{2}\left(\frac{1}{R_{min}} + \frac{1}{R_{max}}\right)$$

if the surface is an eyeball side surface, $$SPH_{mean} = \frac{1-n}{2}\left(\frac{1}{R_{min}} + \frac{1}{R_{max}}\right)$$

a cylinder CYL is also defined by the formula $CYC = |SPH_{max} - SPH_{min}|$.

The characteristics of any aspherical face of the lens may be expressed by the local mean spheres and cylinders. A surface can be considered as locally aspherical when the cylinder is at least 0.25 diopters.

Figure 2:
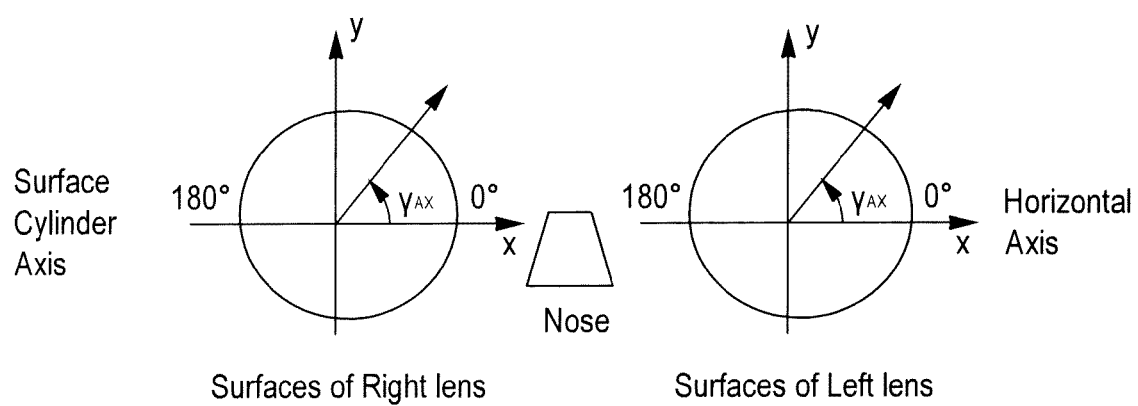
FIG. 2 illustrates the cylinder axis $\gamma_{AX}$ in a convention used to characterize an aspherical surface.

For an aspherical surface, a local cylinder axis $\gamma_{AX}$ may further be defined. FIG. 1 illustrates the astigmatism axis γ as defined in the TABO convention and FIG. 2 illustrates the cylinder axis $\gamma_{AX}$ in a convention defined to characterize an aspherical surface.

The cylinder axis $\gamma_{AX}$ is the angle of the orientation of the maximum curvature $CURV_{max}$ with relation to a reference axis and in the chosen sense of rotation. In the above defined convention, the reference axis is horizontal (the angle of this reference axis is 0°) and the sense of rotation is counter-clockwise for each eye, when looking at the wearer (0°≤$\gamma_{AX}$≤180°). An axis value for the cylinder axis $\gamma_{AX}$ of +45° therefore represents an axis oriented obliquely, which when looking at the wearer, extends from the quadrant located up on the right to the quadrant located down on the left.

Moreover, a progressive multifocal lens may also be defined by optical characteristics, taking into consideration the situation of the person wearing the lenses.

Figure 3:
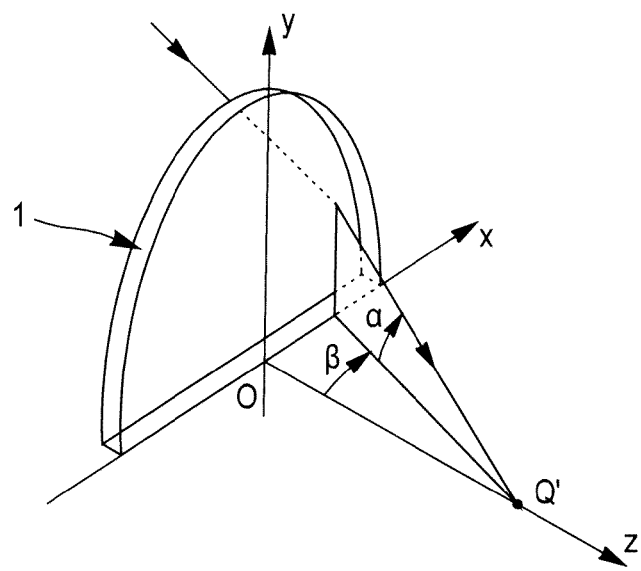
FIGS. 3 and 4 show, diagrammatically, optical systems of eye and lens.
Figure 4:
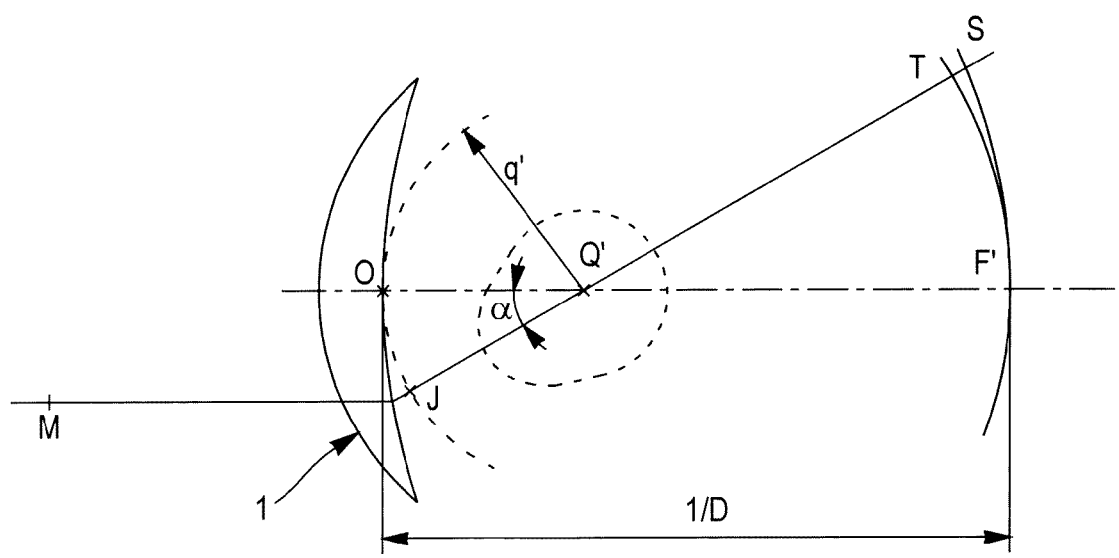

FIGS. 3 and 4 are diagrammatic illustrations of optical systems of eye and lens, thus showing the definitions used in the description. More precisely, FIG. 3 represents a perspective view of such a system illustrating parameters α and β used to define a gaze direction. FIG. 4 is a view in the vertical plane parallel to the antero-posterior axis of the wearer's head and passing through the center of rotation of the eye in the case when the parameter β is equal to 0.

The center of rotation of the eye is labeled Q'. The axis Q'F', shown on FIG. 4 in a dot-dash line, is the horizontal axis passing through the center of rotation of the eye and extending in front of the wearer—that is the axis Q'F' corresponding to the primary gaze view. This axis cuts the aspherical surface of the lens on a point called the fitting cross, which is present on lenses to enable the positioning of lenses in a frame by an optician. The point of intersection of the rear surface of the lens and the axis Q'F' is the point O. O can be the fitting cross if it is located on the rear surface. An apex sphere, of center Q', and of radius q', is tangential to the rear surface of the lens in a point of the horizontal axis. As examples, a value of radius q' of 25.5 mm corresponds to a usual value and provides satisfying results when wearing the lenses.

A given gaze direction—represented by a solid line on FIG. 3—corresponds to a position of the eye in rotation around Q' and to a point J of the apex sphere; the angle β is the angle formed between the axis Q'F' and the projection of the straight line Q'J on the horizontal plane comprising the axis Q'F'; this angle appears on the scheme on FIG. 3. The angle α is the angle formed between the axis Q'J and the projection of the straight line Q'J on the horizontal plane comprising the axis Q'F'; this angle appears on the scheme on FIGS. 3 and 4. A given gaze view thus corresponds to a point J of the apex sphere or to a couple (α, β). The more the value of the lowering gaze angle is positive, the more the gaze is lowering and the more the value is negative, the more the gaze is rising.

In a given gaze direction, the image of a point M in the object space, located at a given object distance, is formed between two points S and T corresponding to minimum and maximum distances JS and JT, which would be the sagittal and tangential local focal lengths. The image of a point in the object space at infinity is formed, at the point F'. The distance D corresponds to the rear frontal plane of the lens.

Ergorama is a function associating to each gaze direction the usual distance of an object point. Typically, in far vision following the primary gaze direction, the object point is at infinity. In near vision, following a gaze direction essentially corresponding to an angle α of the order of 35° and to an angle β of the order of 5° in absolute value toward the nasal side, the object distance is of the order of 30 to 50 cm. For more details concerning a possible definition of an ergorama, U.S. Pat. No. A-6,318,859 may be considered. This document describes an ergorama, its definition and its modeling method. For a method of the invention, points may be at infinity or not. Ergorama may be a function of the wearer's ametropia or wearer's addition.

Using these elements, it is possible to define a wearer optical power and astigmatism, in each gaze direction. An object point M at an object distance given by the ergorama is considered for a gaze direction (α,β). An object proximity ProxO is defined for the point M on the corresponding light ray in the object space as the inverse of the distance MJ between point M and point J of the apex sphere:

ProxO=1/MJ

This enables to calculate the object proximity within a thin lens approximation for all points of the apex sphere, which is used for the determination of the ergorama. For a real lens, the object proximity can be considered as the inverse of the distance between the object point and the front surface of the lens, on the corresponding light ray.

For the same gaze direction (α,β), the image of a point M having a given object proximity is formed between two points S and T which correspond respectively to minimal and maximal focal distances (which would be sagittal and tangential focal distances). The quantity ProxI is called image proximity of the point M:

$$\text{Pr}\,oxI = \frac{1}{2}\left(\frac{1}{JT} + \frac{1}{JS}\right)$$

By analogy with the case of a thin lens, it can therefore be defined, for a given gaze direction and for a given object proximity, i.e. for a point of the object space on the corresponding light ray, an optical power Pui as the sum of the image proximity and the object proximity.

*Pui*=ProxO+ProxI

With the same notations, an astigmatism Ast is defined for every gaze direction and for a given object proximity as:

$$Ast = \left|\frac{1}{JT} - \frac{1}{JS}\right|$$

This definition corresponds to the astigmatism of a ray beam created by the lens. It can be noticed that the definition gives, in the primary gaze direction, the classical value of astigmatism. The astigmatism angle, usually called axis, is the angle γ. The angle γ is measured in the frame $\{Q', x_m, y_m, z_m\}$ linked to the eye. It corresponds to the angle with which the image S or T i formed depending on the convention used with relation to the direction $z_m$ in the plane $\{Q', z_m, y_m\}$.

Possible definitions of the optical power and the astigmatism of the lens, in the wearing conditions, can thus be calculated as explained in the article by B. Bourdoncle et al., entitled "Ray tracing through progressive ophthalmic lenses", 1990 International Lens Design Conference, D. T. Moore ed., Proc. Soc. Photo. Opt. Instrum. Eng.

Figure 5:
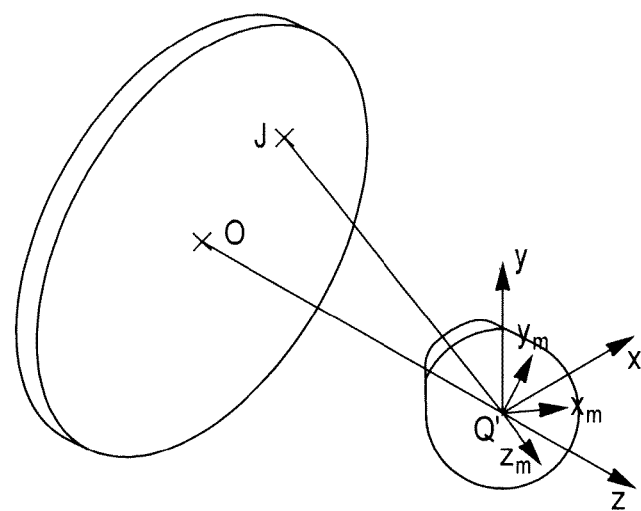
FIG. 5 shows a ray tracing from the center of rotation of the eye.

FIG. 5 represents a perspective view of a configuration wherein the parameters α and β are non zero. The effect of rotation of the eye can thus be illustrated by showing a fixed frame $\{x, y, z\}$ and a frame $\{x_m, y_m, z_m\}$ linked to the eye. Frame $\{x, y, z\}$ has its origin at the point Q'. The axis x is the axis Q'O and it is oriented from the lens toward the eye. The y axis is vertical and oriented upwardly. The z axis is such that the frame $\{x, y, z\}$ be orthonormal and direct. The frame $\{x_m, y_m, z_m\}$ is linked to the eye and its center is the point Q'. The $x_m$ axis corresponds to the gaze direction JQ'. Thus, for a primary gaze direction, the two frames $\{x, y, z\}$ and $\{x_m, y_m, z_m\}$ are the same. It is known that the properties for a lens may be expressed in several different ways and notably in surface and optically. A surface characterization is thus equivalent to an optical characterization. In the case of a blank, only a surface characterization may be used. It has to be understood that an optical characterization requires that the lens has been machined to the wearer's prescription. In contrast, in the case of an ophthalmic lens, the characterization may be of a surface or optical kind, both characterizations enabling to describe the same object from two different points of view. Whenever the characterization of the lens is of optical kind, it refers to the ergorama-eye-lens system described above. For simplicity, the term 'lens' is used in the description but it has to be understood as the 'ergorama-eye-lens system'.

The values in optic terms can be expressed for gaze directions. Gaze directions are usually given by their degree of lowering and azimuth in a frame whose origin is the center of rotation of the eye. When the lens is mounted in front of the eye, a point called the fitting cross is placed before the pupil or before the eye rotation center Q' of the eye for a primary gaze direction. The primary gaze direction corresponds to the situation where a wearer is looking straight ahead. In the chosen frame, the fitting cross corresponds thus to a lowering angle α of 0° and an azimuth angle β of 0° whatever surface of the lens the fitting cross is positioned—rear surface or front surface.

The above description made with reference to FIGS. 3-5 was given for central vision. In peripheral vision, as the gaze direction is fixed, the center of the pupil is considered instead of center of rotation of the eye and peripheral ray directions are considered instead of gaze directions. When peripheral vision is considered, angle α and angle β correspond to ray directions instead of gaze directions.

In the remainder of the description, terms like «up», «bottom», «horizontal», «vertical», «above», «below», or other words indicating relative position may be used. These terms are to be understood in the wearing conditions of the lens. Notably, the "upper" part of the lens corresponds to a negative lowering angle α<0° and the "lower" part of the lens corresponds to a positive lowering angle α>0°. Similarly, the "upper" part of the surface of a lens—or of a semi-finished lens blank—corresponds to a positive value along the y axis, and preferably to a value along the y axis superior to the y_value at the fitting cross and the "lower" part of the surface of a lens—or of a semi-finished lens blank—corresponds to a negative value along the y axis in the frame, and preferably to a value along the y axis inferior to the y_value at the fitting cross.

The wearing conditions are to be understood as the position of the ophthalmic lens with relation to the eye of a wearer, for example defined by a pantoscopic angle, a Cornea to lens distance, a Pupil-cornea distance, a CRE to pupil distance, a CRE to lens distance and a wrap angle.

The Cornea to lens distance is the distance along the visual axis of the eye in the primary position (usually taken to be the horizontal) between the cornea and the back surface of the lens; for example equal to 12 mm.

The Pupil-cornea distance is the distance along the visual axis of the eye between its pupil and cornea; usually equal to 2 mm.

The CRE to pupil distance is the distance along the visual axis of the eye between its center of rotation (CRE) and cornea; for example equal to 11.5 mm.

The CRE to lens distance is the distance along the visual axis of the eye in the primary position (usually taken to be the horizontal) between the CRE of the eye and the back surface of the lens, for example equal to 25.5 mm.

The Pantoscopic angle is the angle in the vertical plane, at the intersection between the back surface of the lens and the visual axis of the eye in the primary position (usually taken to be the horizontal), between the normal to the back surface of the lens and the visual axis of the eye in the primary position; for example equal to −8°.

The wrap angle is the angle in the horizontal plane, at the intersection between the back surface of the lens and the visual axis of the eye in the primary position (usually taken to be the horizontal), between the normal to the back surface of the lens and the visual axis of the eye in the primary position for example equal to 0°.

An example of wearer condition may be defined by a pantoscopic angle of −8°, a Cornea to lens distance of 12 mm, a Pupil-cornea distance of 2 mm, a CRE to pupil distance of 11.5 mm, a CRE to lens distance of 25.5 mm and a wrap angle of 0°.

Other conditions may be used. Wearing conditions may be calculated from a ray-tracing program, for a given lens.

As indicated previously, the gaze directions are usually defined from the center of rotation of the eye of the wearer.

Figure 6:
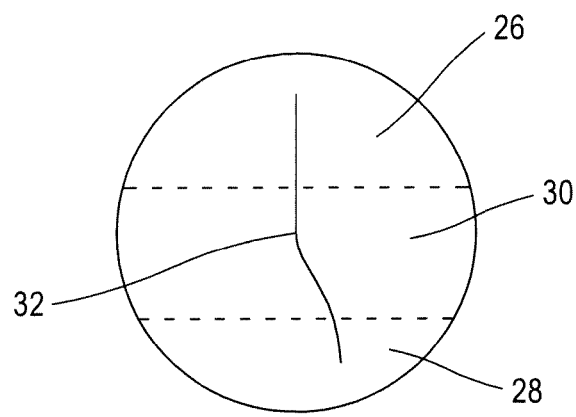
FIGS. 6 and 7 show field vision zones of a lens.
Figure 7:
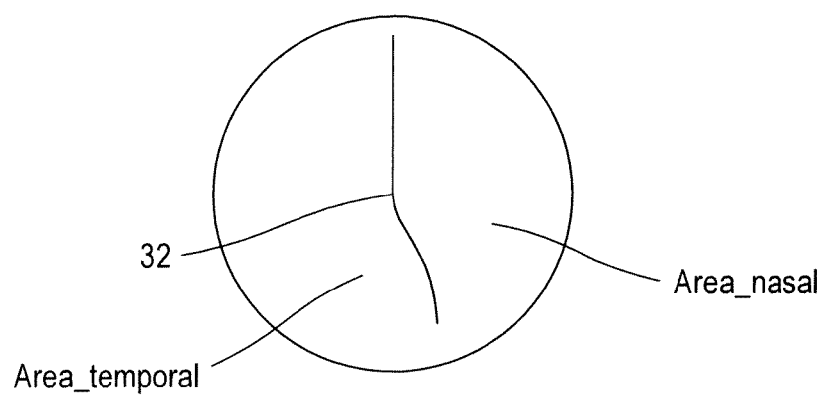

The visual field zones seen through a lens are schematically illustrated in FIGS. 6 and 7. The lens comprises a far vision zone 26 located in the upper part of the lens, a near vision zone 28 located in the lower part of the lens and an intermediate zone 30 situated in the lower part of the lens between the far vision zone 26 and the near vision zone 28. The lens also has a main meridian 32 passing through the three zones and defining a nasal side and a temporal side.

For the purpose of the invention, the meridian line 32 of a progressive lens is defined as follow: for each lowering of the view of an angle $\alpha=\alpha_1$ between the gaze direction corresponding to the fitting cross and a gaze direction being in the near vision zone, the gaze direction $(\alpha_1, \beta_1)$ is searched for which the local residual astigmatism is minimum. Thus, all the gaze directions defined in that way form the meridian line of the ergorama-eye-lens system. The meridian line of the lens represents the locus of mean gaze directions of a wearer when he is looking from far to near visions. The meridian line 32 of a surface of the lens is defined as follows: each gaze direction $(\alpha, \beta)$ belonging to the optical meridian line of the lens intersects the surface at a point (x, y). The meridian line of the surface is the set of points corresponding to the gaze directions of the meridian line of the lens.

As shown in FIG. 7, the meridian 32 separates the lens into a nasal area and a temporal area. As expected, the nasal area is the area of the lens which is between the meridian and the nose of the wearer whereas the temporal area is the area which is between the meridian and the temple of the wearer. The nasal area is labeled Area_nasal and the temporal area is labeled Area_temporal, as it will in the remainder of the description.

The invention relates to a method, for example implemented by computer means, for determining an ophthalmic lens having unwanted astigmatism, the ophthalmic lens being adapted to a wearer.

Figure 8:
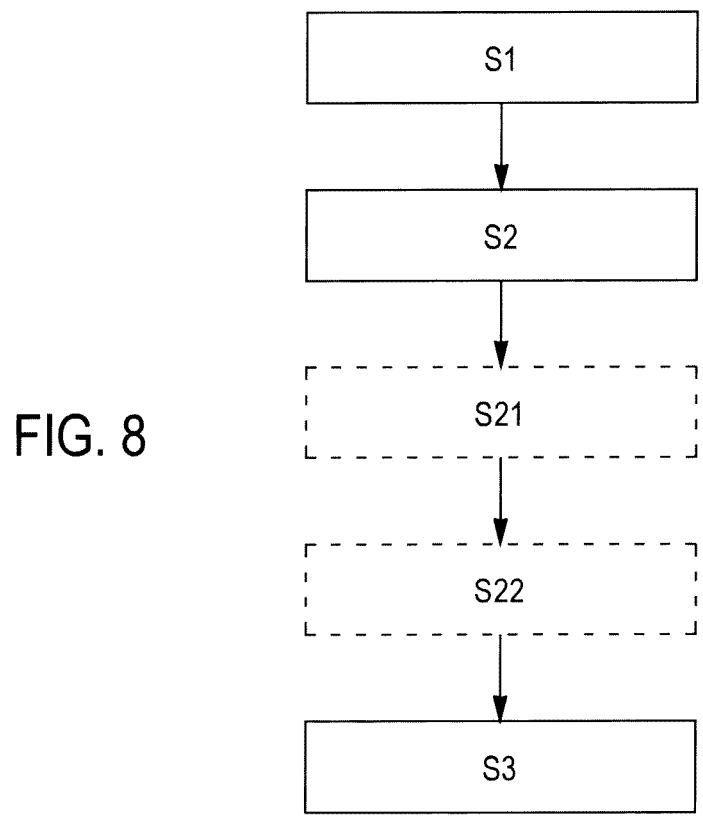
FIG. 8 is an illustration of a chart-flow of an embodiment of the method according to the invention.

As represented on FIG. 8, the method according to the invention comprises at least:
  a wearer prescription data providing step S1,
  a wearer focal data providing step S2, and
  a ophthalmic lens determining step S3.

During the wearer prescription data providing step S1, wearer prescription data indicative of the ophthalmic prescription of the wearer are provided. Typically, the ophthalmic prescription of the wearer is provided. Alternatively information allowing determining such ophthalmic prescription may be provided, for example an indication allowing determining the ophthalmic prescription of the wearer from a data base may be provided.

The ophthalmic prescription of a wearer is a set of optical characteristics of optical power, of astigmatism and, where relevant, of addition, determined by an ophthalmologist in order to correct the vision defects of an individual, for example by means of a lens positioned in front of his eye. Generally speaking, the prescription for a progressive addition lens comprises values of spherical power and of astigmatism at the distance-vision point and, where appropriate, an addition value.

According to an embodiment of the invention, the prescription of the wearer comprises a cylinder prescription value and/or a cylinder prescription axis value and/or a sphere prescription value.

During the wearer focal data providing step S2, wearer focal data indicative of the wearer preferred image focal plan are provided. Typically, the wearer preferred image focal plan is provided, in particular the position of the preferred image focal plan of the wearer. Alternatively information allowing determining such wearer preferred image focal plan may be provided, for example an indication allowing determining the wearer preferred image focal plan in a data base may be provided.

As indicated previously, such position of the preferred image focal plan of the wearer may be any position within the Sturm's interval.

Figure 9:
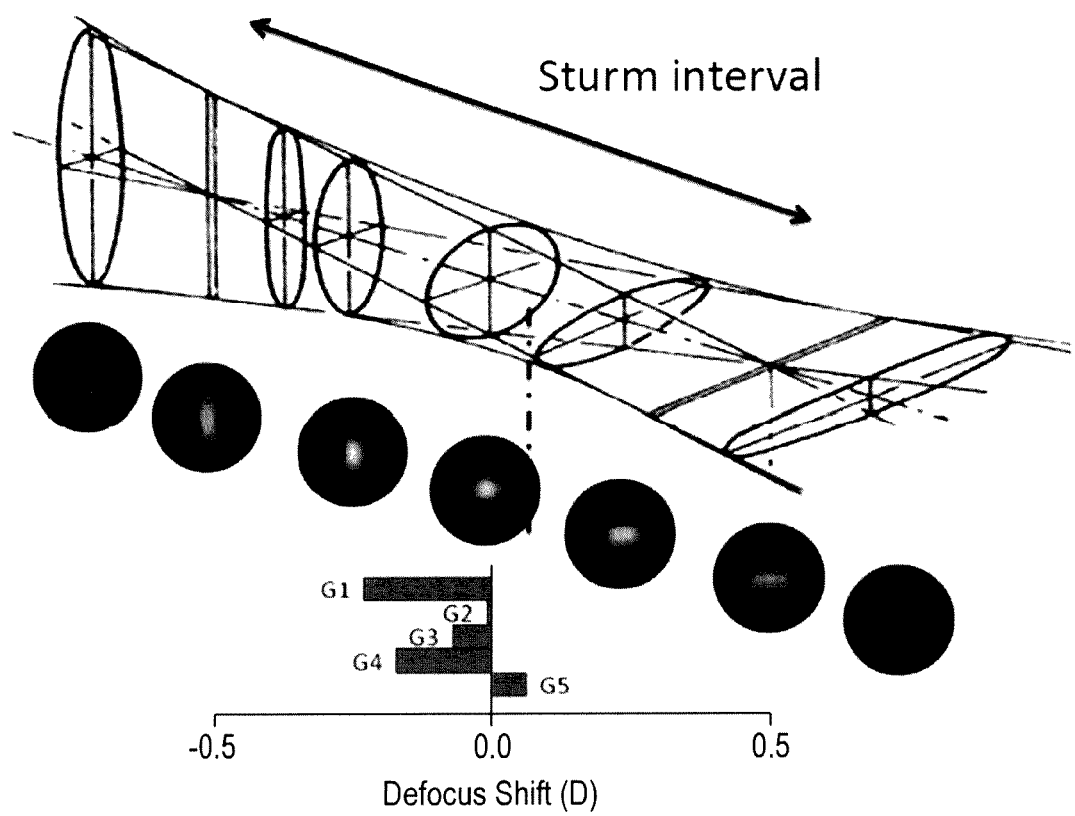
FIG. 9 illustrates the defocused patch of light produced by a sphero-toric lens within the Sturm interval.

As illustrated on FIG. 9, the shape of the defocused patch of light produced by a sphero-toric lens varies within the Sturm interval from a vertical line, to a vertical ellipses, to a circle, to horizontal ellipses and then to a horizontal line.

FIG. 9 show the ray beam through the Sturm interval in the presence of 1 D of astigmatism, as well as the resulting image of a punctual object for various focal plan corresponding to different defocus shift. The horizontal bar graph correspond to the mean image focal plan obtain experimentally for 5 different groups of subjects. The reference position (0 defocus shift) corresponds to the circle of least confusion. When a subject prefers a position of the image focal plan corresponding to a resulting vertical image (due to a better focalization of horizontal rays compared to vertical rays, as this is the case in the left part of the figure), the subject is said to have a vertical preference (as for subjects of groups 1 and 4 and to a lesser extent group 3). When a subject prefers a position of the image focal plan corresponding to a resulting horizontal image (due to a better focalization of vertical rays compared to horizontal rays, as this is the case in the right part of the figure), the subject is said to have a horizontal preference (as for subjects of group 5). Subjects from group 2 prefer a position of the image focal plan almost on the circle of least confusion meaning they have no orientation preference.

The preferred image focal plan of the wearer when wearing an ophthalmic lens having unwanted astigmatism, may be determined by a method according to the invention. The method comprises:

an "unwanted astigmatism" providing step
a wearer preferred image focal plan position determining step A mean generating astigmatism of a specific amount is provided to the wearer during the "unwanted astigmatism" providing step. This astigmatism is provided in addition to an eventual astigmatism correction corresponding to the prescription of the wearer, creating thus the equivalent of an unwanted astigmatism.

An optical lens having controlled cylinder power may be used to provide "unwanted astigmatism" to the wearer during the "unwanted astigmatism" providing step. For example, a value of 1 D, horizontal or vertical, may be used. Alternatively, any other value and orientation may be used.

During the wearer preferred image focal plan position determining step the position of the wearer preferred image focal plan is determined by adjusting the position of the image plan until the position indicated by the wearer as preferred is reached. The position of the image plan can be adjusted for example modifying the spherical power provided to the wearer.

The wearer preferred image focal plan position determining step may be repeated without the provided unwanted astigmatism, to determine the reference position. The difference between the two positions may be provided as for the wearer focal data indicative of the wearer preferred image focal plan.

The difference between the spherical power measured with and without provided unwanted astigmatism corresponds to the wearer focal data (WFD).

The adjustment of the position of the image-plan may be done by controlling the spherical power of the optical lens.

More generally to determine the wearer focal data requires:

A way to generate astigmatism such as a test glass 1 D astigmatism at 0° or an active system such as active lenses or deformable mirror or a phoropter.

A means of varying the focus such as test lenses, a Badal system comprising movable flat mirror and a lens, an active system with a variable power lens or a deformable mirror, a displacement of the object being viewed, and A return of the subject, either subjective (preference or direct control of the development) or objective (direct measure of accommodation).

Experimental Set-Up Used by the Inventors

An electromagnetic deformable mirror (52 actuators and a 50-μm stroke; MIRAO, Imagine Eyes, France) was used to induce astigmatism and correct the aberration of the subject. Focus correction was achieved by means of a Badal system mounted on a linear motor stage.

Best-Focus Search Method

A best-focus search algorithm, based on interleaved staircases, was used. The algorithm is based on a randomized-step efficient method, where the subject reports (using a two buttons in a keyboard) whether a gray-scale image presented in the display appears more blurred or sharper than the precedent image. The maximum number of trials in each staircase was 30, and best focus was selected after a maximum number of 11 reversals. Four staircases are interleaved with different initial values [−0.75 D, −0.50 D, +0.50 D, +0.75 D] from an initial focus setting. The subject's responses may be beyond the interval given by the initial settings. Best focus is defined as the average of the last 8 reversals. Focus positions during the trial are automatically set by means of the motorized Badal system, according to the subject's responses. For each experimental condition, best-focus search was performed using four different image types (oblique black E letter on a white background; an image of a face; an urban landscape; and an image of fruits).

Experimental Protocol

Astigmatism was always induced by the same amount (+1 D) and at the isotropic focus of the Sturm interval. Subjects were dilated with tropicamide 1%, two drops 10 min apart at the beginning of the experiment and then every 60 min to ensure paralyzed accommodation during the measurements. Following dilation, the eye's natural pupil was aligned to the optical axis of the instrument, with stabilization guaranteed by the use of a dental impression. The deformable mirror was set to compensate for the natural aberrations of the subject. The subject performed a subsequent manual subjective focus setting. This setting was used as a base-line for the staircase-based best-focus search. This staircase-based best-focus was repeated both under aberrations corrected without and with induced "unwanted astigmatism". The same procedure was repeated for the four different images used in the experiment.

During the ophthalmic lens determining step S3, the ophthalmic lens is determined based on the prescription of the wearer and the wearer focal data so as to reduce the impact of the unwanted astigmatism of the ophthalmic lens for the wearer.

According to an embodiment of the invention, the spherical power of the ophthalmic lens is determined based on the prescription of the wearer and the position of the wearer preferred image focal plan so as to reduce the impact of the unwanted astigmatism of the ophthalmic lens for the wearer.

For example, for each gaze direction $(\alpha i, \beta i)$ for which the ophthalmic lens has unwanted astigmatism, the spherical power of the ophthalmic lens is determined so that the distance between the wearer preferred image focal plan and the retina of the wearer is reduced. Preferably, for each gaze direction $(\alpha i, \beta i)$ for which the ophthalmic lens has unwanted astigmatism, the spherical power of the ophthalmic lens is determined so that the wearer preferred image focal plan corresponds to the retina of the wearer.

By retina it is understood any surfaces optically conjugated with the retina. It may be either the real retina of the subject. In such a case, reducing the distance between the wearer preferred image focal plan and the retina of the wearer must take into account the geometry of the eye of the wearer or a model of it. Advantageously, the calculation can be made for surfaces conjugated to the retina outside the eye. Such surfaces are represented on FIG. 4 by the spheres going through point F'. These surfaces are commonly derived from the prescription. In such a case, reducing the distance with the wearer preferred image focal plan is achieved without the need of the geometry nor a model of the eye.

According to an embodiment of the invention where the ophthalmic lens has an unwanted astigmatism of horizontal axis in at least one gaze direction $(\alpha i, \beta i)$, during the ophthalmic lens determining step for the at least one gaze direction $(\alpha i, \beta i)$:

the spherical power of the ophthalmic lens is increased relative to spherical power based on the ophthalmic prescription of the wearer when the wearer preferred image focal plan corresponds to a vertical preference; and the spherical power of the ophthalmic lens is reduced relative to spherical power based on the ophthalmic prescription of the wearer when the wearer preferred image focal plan corresponds to a horizontal preference.

Such embodiment is to be understood with a positive cylinder convention wherein the astigmatism is indicated in positive power. The horizontal and vertical directions are to be understood as defined in the Tabo convention.

According to an embodiment of the invention where the ophthalmic lens has an unwanted astigmatism of vertical axis in at least one gaze direction $(\alpha i, \beta i)$, during the ophthalmic lens determining step for the at least one gaze direction $(\alpha i, \beta i)$:

the spherical power of the ophthalmic lens is reduced relative to spherical power based on the ophthalmic prescription of the wearer when the wearer preferred image focal plan corresponds to a vertical preference; and the spherical power of the ophthalmic lens is increased relative to spherical power based on the ophthalmic prescription of the wearer when the wearer preferred image focal plan corresponds to a horizontal preference.

Such embodiment is to be understood with a positive cylinder convention wherein the astigmatism is indicated in positive power. The horizontal and vertical directions are to be understood as defined in the Tabo convention.

As illustrated on FIG. 8, according to an embodiment of the invention, the method may further comprise prior to the ophthalmic lens determining step S3:

an initial optical function Fi providing step S21, and
an target optical function determining step S22.

During the initial optical function Fi providing step an initial optical function is provided. The initial optical function comprises for each gaze direction $(\alpha i, \beta i)$ of a set of gaze directions S $((\alpha 1, \beta 1); (\alpha 2, \beta 2); \ldots ; (\alpha n, \beta n))$, at least a value of unwanted astigmatism ASRi and a value of spherical power Pi is provided. Typically, the initial optical function is determined based on the ophthalmic prescription of the wearer using existing optical design determining methods.

During the target optical function determining step a target optical function Ft is determined. The target optical function comprises for each gaze direction $(\alpha i, \beta i)$ of a set of gaze directions S $((\alpha 1, \beta 1); (\alpha 2, \beta 2); \ldots ; (\alpha n, \beta n))$, a target value of unwanted astigmatism ASRt and a target value of spherical power Pt with ASRt=ASRi and Pt=Pi+Corr, Corr being a spherical power corrective value based at least on the wearer focal data provided during the wearer focal data providing step.

During the ophthalmic lens determining step the ophthalmic lens is determined based on the target optical function.

The spherical power corrective value Corr may be defined as a function of a target of unwanted astigmatism, the target of unwanted astigmatism defined as the difference between the astigmatism of the ophthalmic lens and the astigmatism of the ophthalmic prescription of the wearer. Corr=f(CYLcib), for example Corr=CYLcib This function can also be weighted by a function of the wearer focal data WFD.

$$Corr=f(CYLcib)*g(WFD)$$

For example, if the difference between the two positions as measured in the example of step S2 with and without an unwanted astigmatism ASTmes is provided for the wearer focal data indicative of the wearer preferred image focal plan, $$g(WFD)=WFD/ASTmes$$

The inventors have shown that subjects shift their preferred focal plane in the presence of astigmatism of a value dependent on their prescription. Indeed, the 5 groups of subjects represented in FIG. 9 correspond to particular limitation groups: G1: emmetropic, G2: myopic G3 hyperopic, G4: astigmatism at 0° (horizontal), G5: astigmatism 90° (vertical in Tabo). The observed result is that emmetropic have a vertical preference in the presence of astigmatism, ametropes remain close to circle of least confusion corresponding to a zero shift from the best focus without astigmatism, astigmatism groups shift in opposite directions, corresponding to a preference having a direction related to their natural astigmatism.

Figure 10:
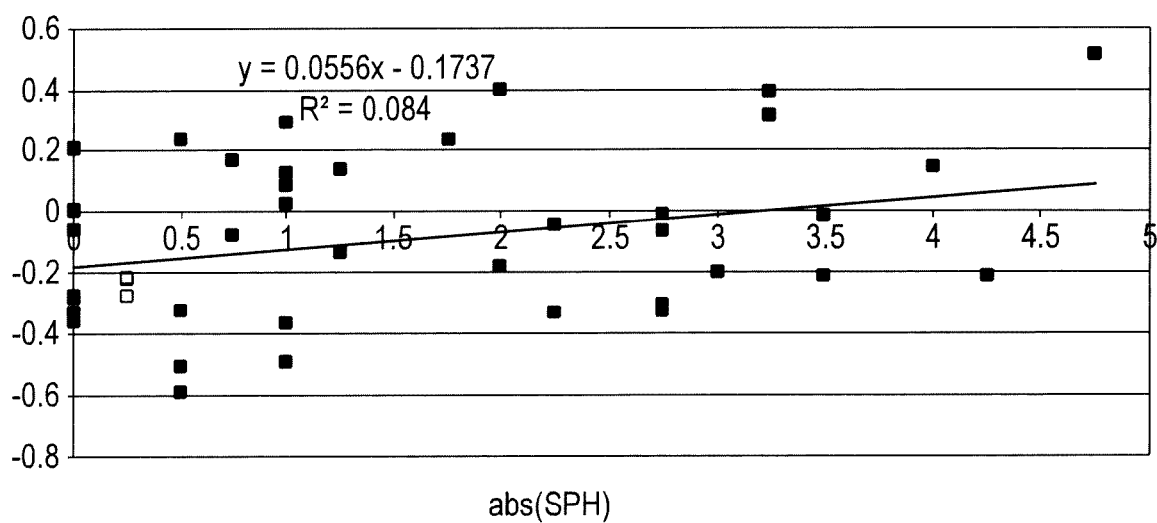
FIG. 10 represents the value of the shift obtained as a function of the absolute value of the spherical power of the prescription.
Figure 11:
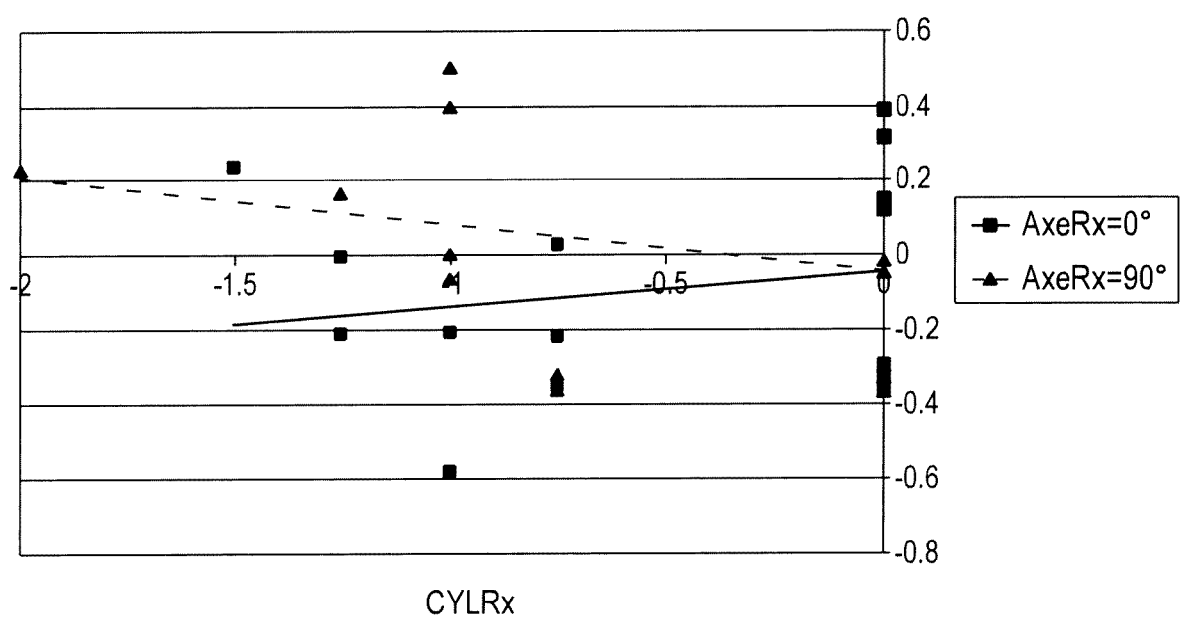
FIG. 11 represents the shift value obtained as a function of the value of the cylinder of the prescription of astigmatic groups.

More specifically, the shift can be estimated as linearly proportional to the ametropia and astigmatism prescription of the subjects as illustrated in FIGS. 10 and 11.

FIG. 10 represents the value of the shift obtained as a function of the absolute value of the spherical power of the prescription of the subjects.

FIG. 11 represents the shift value obtained as a function of the value of the cylinder of the prescription of each of the two astigmatic groups.

It is observed that the measured shift of the position of the preferred plan may be approximated by functions of the wearer's prescription.

For example, for an ophthalmic prescription defined by (SPH, $Cyl_{Rx}$, $axe_{Rx}$) and target of unwanted astigmatism defined by ($CYL_{cib}$, $axe_{cib}$), the spherical power corrective value Corr can be defined as:

$$Corr = f(CYL_{cib}) * g(|SPH|, Cyl_{Rx}, axe_{Rx}, axe_{cib})$$

The function g can be likened to a coefficient of sensitivity, customizable for each wearer from at least one measurement of Corr for a given cylinder value.

The inventors have established the following formula based on experimental results:

$$Corr = -CYL_{cib} * \{(-0.175+0.056*|SPH|)*\cos(2*[axe_{cib}-axe_{Rx}]))+0.1*CYL_{Rx}*\cos(2*[axe_{cib}-axe_{Rx}])\} \text{ if } 0.056*|SPH| \leq 0.175 \text{ and}$$

$$Corr = -CYL_{cib} * \{0.1*CYL_{Rx}*\cos(2*[axe_{cib}-axe_{Rx}])\} \text{ if } 0.056*|SPH| \geq 0.175$$

Figure 12A:
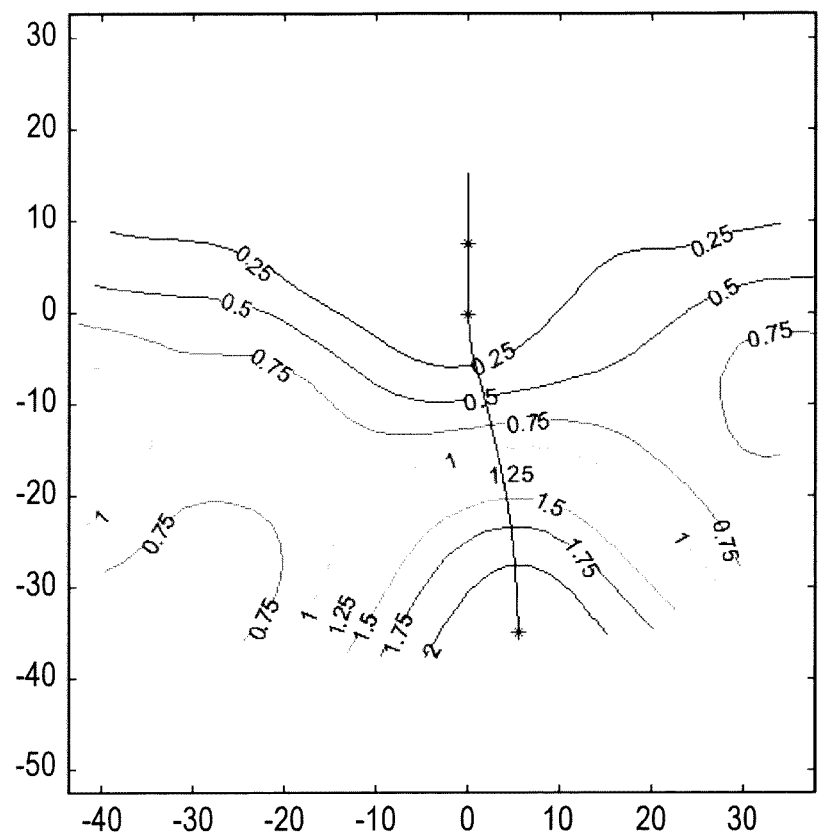
FIGS. 12 to 14 illustrate examples of implementation of the method according to the invention.
Figure 12B:
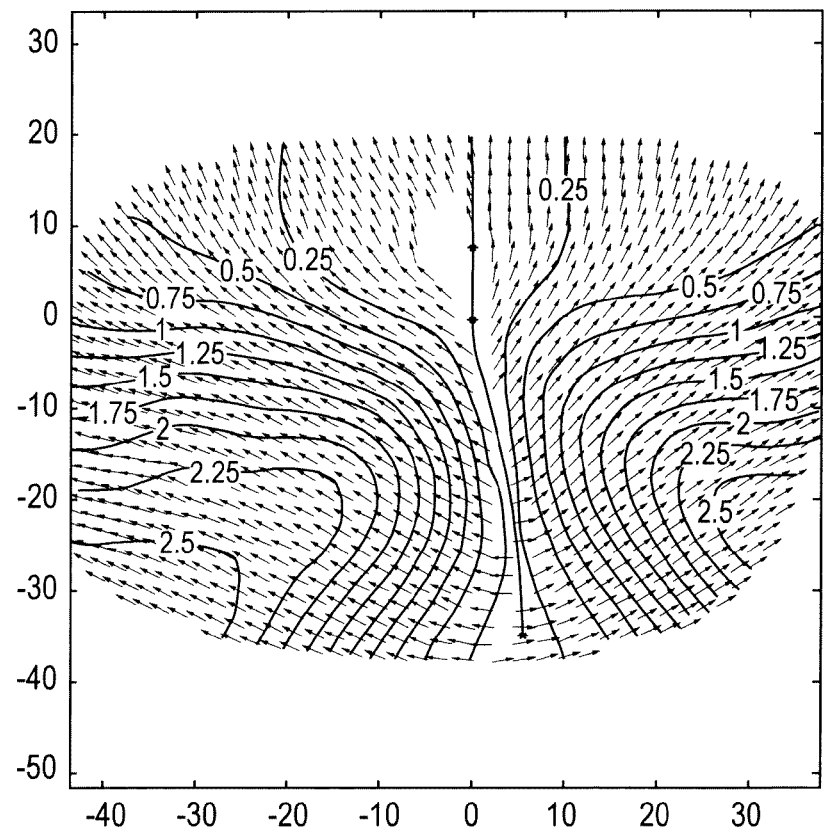

FIGS. 12a to 12b show features of a plano standard progressive addition of 2 D of addition.

FIG. 12a shows lines of equal spherical power, i.e. lines formed by points for which the spherical power has an identical value. The x-axis and y-axis give the coordinates corresponding to the view angle ($\alpha i, \beta i$) in degree.

FIG. 12b shows, using the same axes as for FIG. 12b, lines of equal cylinder, and the arrows on FIG. 12b show the direction of the axis.

Figure 13A:
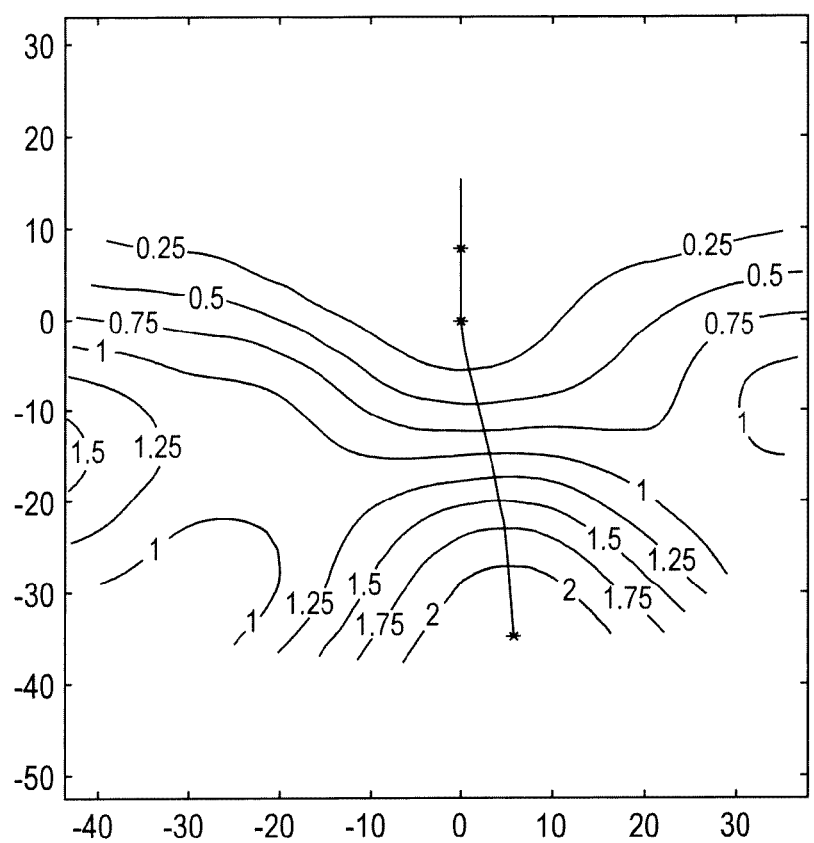

FIGS. 13a shows lines of equal spherical power with a spherical power shift determined using a method of the invention based on the astigmatism values represented on FIG. 12b.

Figure 13B:
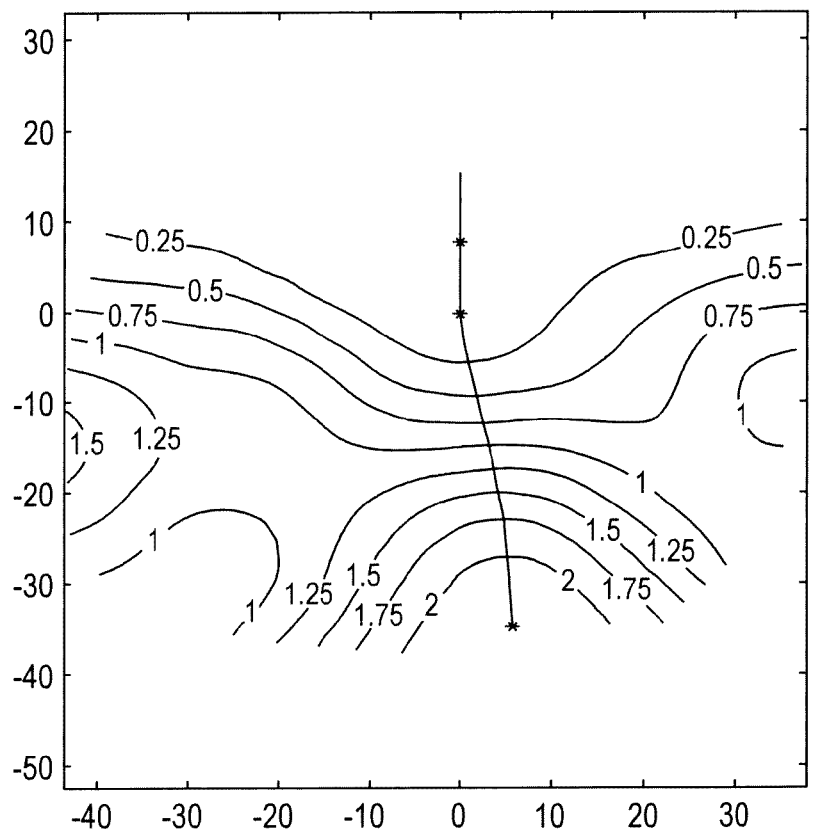

FIG. 13b shows the shift of spherical power, by subtracting the spherical power of FIG. 13a with FIG. 12a. The cylinder and astigmatism of the new ophthalmic lens is unchanged.

Figure 14:
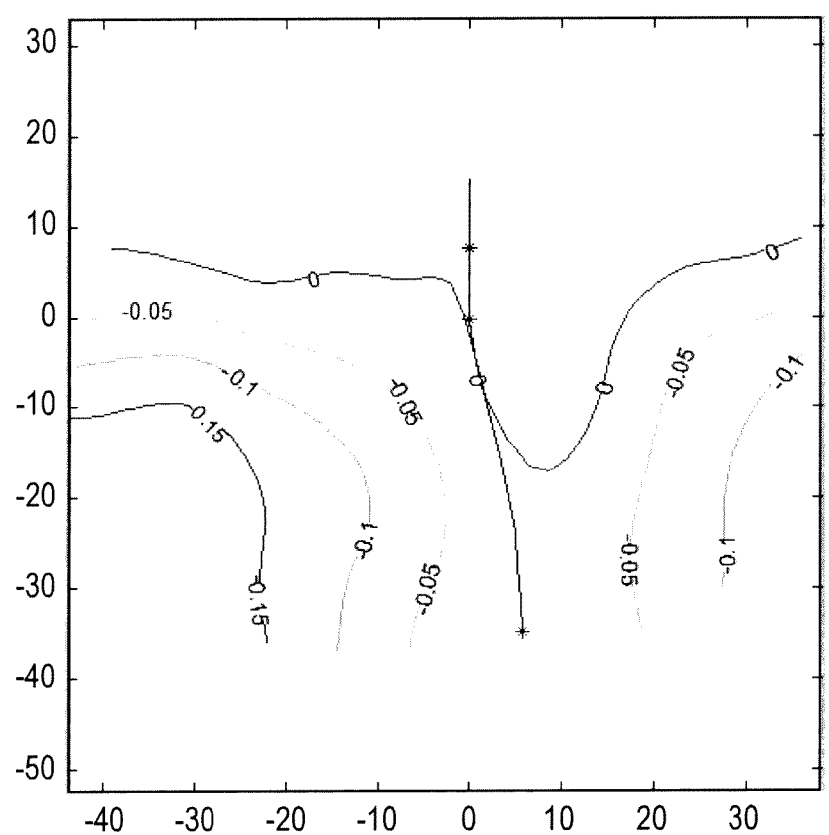

FIG. 14 shows an example of spherical power shift determined for a initial ophthalmic lens corresponding to a prescription of SPH=-4 D, $CYLR_x$=-1 D $axeRx$=90°.

Since $|SPH| \geq 3.125$ D, the spherical power corrective value is calculated:

$$Corr = -CYLcib * \{0.1*CYLRx*\cos(2*[axecib-axeRx])\}$$

i.e. $Corr = -0.1*CYLcib*\cos(2*axecib)$

The invention also relates to a set of ophthalmic lenses having the same prescription, i.e. adapted to provide the same ophthalmic correction, the set of ophthalmic lenses comprising at least a first ophthalmic lens and a second ophthalmic lens.

For each gaze direction ($\alpha i, \beta i$) the difference of unwanted astigmatism between the first and second ophthalmic lenses is smaller than or equal to 0.12 D. In other words for each gaze direction ($\alpha i, \beta i$) the unwanted astigmatism is substantially the same for the first and second ophthalmic lenses.

Over a group of gaze directions corresponding for each of the first and second ophthalmic lenses, to an unwanted astigmatism greater than 0.75 D, the difference of spherical power between the first and second ophthalmic lenses is greater than or equal to 0.12 D. In other words, one of the ophthalmic lenses has been adapted according to the method of the invention so as to reduce the impact of the unwanted astigmatism of the ophthalmic lens for the wearer whereas the other has been determined without adapting the spherical power to reduce the impact of the unwanted astigmatism of the ophthalmic lens for the wearer.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method for determining an ophthalmic lens having unwanted astigmatism, the ophthalmic lens being adapted to a wearer, the method comprising:
   a wearer prescription data obtaining step, performed by a processor of a computer, during which wearer prescription data indicative of an ophthalmic prescription of the wearer are obtained;
   a wearer focal data obtaining step, performed by the processor, during which wearer focal data indicative of a wearer preferred image focal plane are obtained; and
   an ophthalmic lens determining step, performed by the processor, during which a spherical power of the ophthalmic lens is determined based on the ophthalmic prescription of the wearer and focal data of the wearer to reduce impact of unwanted astigmatism of the ophthalmic lens for the wearer in at least one gaze direction, wherein
   the wearer focal data obtaining step obtains the wearer focal data as a result of:
      generating astigmatism using a test glass 1 D astigmatism at 0° or active lenses or deformable mirror or a phoropter, and
      varying focus by test lenses, a Badal system comprising a movable flat mirror and a lens, an active system with a variable power lens or a deformable mirror, a displacement of the object being viewed.

2. The method according to claim 1, wherein during the ophthalmic lens determining step the spherical power of the ophthalmic lens is determined so that a distance between the preferred image focal plane of the wearer and a retina of the wearer is reduced.

3. The method according to claim 1,
   wherein the ophthalmic lens has an unwanted astigmatism of horizontal axis in the at least one gaze direction, and
   wherein during the ophthalmic lens determining step for the at least one gaze direction:
      a spherical power of the ophthalmic lens is increased relative to spherical power based on the ophthalmic prescription of the wearer when the preferred image focal plane of the wearer corresponds to a vertical preference, and
      the spherical power of the ophthalmic lens is reduced relative to spherical power based on the ophthalmic prescription of the wearer when the preferred image focal plane of the wearer corresponds to a horizontal preference.

4. The method according to claim 1,
wherein the ophthalmic lens has an unwanted astigmatism of vertical axis in the at least one gaze direction, and
wherein during the ophthalmic lens determining step for the at least one gaze direction:
   a spherical power of the ophthalmic lens is reduced relative to spherical power based on the ophthalmic prescription of the wearer when the preferred image focal plane of the wearer corresponds to a vertical preference, and
   the spherical power of the ophthalmic lens is increased relative to spherical power based on the ophthalmic prescription of the wearer when the preferred image focal plane of the wearer corresponds to a horizontal preference.

5. The method according to claim 1, further comprising:
an initial optical function obtaining step, performed by the processor, during which an initial optical function comprising for each gaze direction of a set of gaze directions, a value of unwanted astigmatism ASRi, and a value of spherical power Pi are obtained; and
a target optical function determining step, performed by the processor, during which an target optical function comprising for each gaze direction of a set of gaze directions, a target value of unwanted astigmatism ASRt, and a target value of spherical power Pt are determined, with ASRt=ASRi and Pt=Pi+Corr,
   Corr being a spherical power corrective value based at least on the wearer focal data; and
   during the ophthalmic lens determining step the ophthalmic lens is determined based on the target optical function.

6. The method according to claim 5,
wherein the wearer prescription data comprises a cylinder prescription value, and
wherein the spherical power corrective value Corr is determined based at least on the cylinder prescription value.

7. The method according to claim 5,
wherein the wearer prescription data comprises a cylinder prescription axis value, and
wherein the spherical power corrective value Corr is determined based at least on the cylinder prescription axis value.

8. The method according to claim 5,
wherein the wearer prescription data comprises a sphere prescription value, and
wherein the spherical power corrective value Corr is determined based at least on the sphere prescription value.

9. The method according to claim 1, wherein
during the ophthalmic lens determining step the spherical power of the ophthalmic lens in the at least one gaze direction is determined based on the ophthalmic prescription of the wearer and a position of the preferred image focal plane of the wearer to reduce the impact of the unwanted astigmatism of the ophthalmic lens for the wearer.

10. A method for determining a wearer preferred image focal plane when wearing an ophthalmic lens having unwanted astigmatism, the method comprising:
   an unwanted astigmatism obtaining step, performed by a processor of a computer, during which a mean generating astigmatism of a specific amount is obtained from the wearer; and
   a wearer preferred image focal plane position determining step, performed by the processor, during which a position of the preferred image focal plane of the wearer is determined by adjusting a position of the image plane, by modifying the spherical power provided to the wearer, until a position indicated by the wearer as preferred is reached.

11. A set of ophthalmic lenses having a same prescription, the set of ophthalmic lenses comprising at least a first ophthalmic lens and a second ophthalmic lens, wherein:
   for each gaze direction a difference of unwanted astigmatism between the first and the second ophthalmic lenses is smaller than or equal to 0.12D, and
   over a group of gaze directions corresponding for each of the first and the second ophthalmic lenses, to an unwanted astigmatism greater than 0.75 D, a difference of spherical power between the first and the second ophthalmic lenses is greater than or equal to 0.12D.

12. A system for determining an ophthalmic lens having unwanted astigmatism adapted to a wearer, comprising:
   a non-transitory computer-readable medium having computer program instructions stored thereon, which when executed by at least one processor cause the at least one processor to perform the following steps:
      receive wearer prescription data indicative of an ophthalmic prescription of the wearer,
      receive wearer focal data indicative of a preferred image focal plane of the wearer, and
      determine the ophthalmic lens based on the ophthalmic prescription of the wearer and the wearer focal data to reduce impact of the unwanted astigmatism of the ophthalmic lens for the wearer, wherein
   the wearer focal data is received as a result of:
      generating astigmatism using a test glass 1D astigmatism at 0° or active lenses or deformable mirror or a phoropter, and
      varying focus by test lenses, a Badal system comprising a movable flat mirror and a lens, an active system with a variable power lens or a deformable mirror, a displacement of the object being viewed.

* * * * *